(12) United States Patent
Butzine

(10) Patent No.: US 7,364,358 B1
(45) Date of Patent: Apr. 29, 2008

(54) SYSTEM AND METHOD FOR X-RAY SYSTEM STATUS INDICATION

(75) Inventor: Jonathan Mark Butzine, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/553,052

(22) Filed: Oct. 26, 2006

(51) Int. Cl.
*H05G 1/00* (2006.01)
(52) U.S. Cl. .................. 378/204; 378/117; 378/210
(58) Field of Classification Search .............. 378/114, 378/117, 193–198, 204, 210
See application file for complete search history.

(56) References Cited

U.S. PATENT DOCUMENTS 7,239,685 B2 * 7/2007 Petrick et al. .............. 378/116

* cited by examiner

*Primary Examiner*—Courtney Thomas
(74) *Attorney, Agent, or Firm*—Cantor Colburn LLP

(57) ABSTRACT

A status indication device configured for use in an x-ray system is disclosed. The device includes an audio receiver, a processor, a tone generator, and an adjustment mechanism. The audio receiver is configured and disposed to collect audio information surrounding the x-ray system. The processor is coupled to the audio receiver and receptive of a signal representative of the collected audio information. The tone generator is coupled and responsive to the processor and is configured to generate an audio tone in response to a defined status of the x-ray system. The adjustment mechanism is coupled to the tone generator and the processor and dynamically develops a set of audio properties that cause the audio tone to be distinguishable from the collected audio information.

23 Claims, 3 Drawing Sheets

SYSTEM AND METHOD FOR X-RAY SYSTEM STATUS INDICATION

BACKGROUND OF THE INVENTION

The present disclosure relates generally to x-ray system status indication, and particularly to x-ray system status tone generation.

Some x-ray systems rely on a tone and a light to indicate that an x-ray exposure is in progress. X-ray systems, such as a mobile x-ray system, for example, may be utilized in many environments such as hospitals that may include other devices that generate audio tones, such as from multiple alarms or monitors, as well as ambient background noise that may be generated by ventilators, and intravenous pumps, for example. Mobile x-ray systems may be used in many different rooms having various types and levels of background noise, such as an intensive care unit, an operating room, an emergency room, and a neo-natal care room, for example.

In these environments it can be difficult to distinguish the tone generated in response to the x-ray exposure from other noises in the room. Depending upon the type and intensity of ambient noise within the room in which the x-ray system is used, the specific tone that relates to the exposure of the x-ray system may be difficult to distinguish. Although the volume of the tone may be turned to a volume loud enough to be louder than the other noises in a room, the user may not want the volume that high in all circumstances, such as if an x-ray is taken to determine that a breathing tube is properly positioned within a sleeping patient, for example. If an operator of the x-ray system does not understand that the exposure has occurred, he or she may decide to re-take the exam, which would potentially result in an image that does not conform to expectations.

Accordingly, there is a need in the art for an x-ray status indication arrangement that overcomes these drawbacks.

BRIEF DESCRIPTION OF THE INVENTION

An embodiment of the invention includes a status indication device configured for use in an x-ray system. The device includes an audio receiver, a processor, a tone generator, and an adjustment mechanism. The audio receiver is configured and disposed to collect audio information surrounding the x-ray system. The processor is coupled to the audio receiver and receptive of a signal representative of the collected audio information. The tone generator is coupled and responsive to the processor and is configured to generate an audio tone in response to a defined status of the x-ray system. The adjustment mechanism is coupled to the tone generator and the processor and dynamically develops a set of audio properties that cause the audio tone to be distinguishable from the collected audio information.

Another embodiment of the invention includes an x-ray system having an x-ray tube assembly configured to transmit x-ray radiation and an x-ray detector assembly positioned opposite the x-ray tube assembly for detection of x-rays transmitted through a subject. The system also includes an audio receiver, a processor, a tone generator, and an adjustment mechanism. The audio receiver is configured and disposed to collect audio information surrounding the x-ray system. The processor is coupled to the audio receiver and receptive of a signal representative of the collected audio information. The tone generator is coupled and responsive to the processor and is configured to generate an audio tone in response to a defined status of the x-ray system. The adjustment mechanism is coupled to the tone generator and the processor and dynamically develops a set of audio properties that cause the audio tone to be distinguishable from the collected audio information.

Another embodiment of the invention includes a system for use in an x-ray system including means for receiving audio information surrounding and associated with the x-ray system and means for processing the audio information receptive of a signal representative of the collected audio information. The system further includes means for generating an audio tone responsive to the processing means in response to a defined status of the x-ray system, and means for adjusting the audio tone by developing a set of audio properties that cause the audio tone to be distinguishable from the collected audio information.

Another embodiment of the invention includes a method including receiving audio information surrounding and associated with the x-ray system, processing the audio information, and generating an audio tone responsive to the processing of the audio information. The method also includes adjusting the audio tone to be distinguishable from the received audio information.

BRIEF DESCRIPTION OF THE DRAWINGS

Referring to the exemplary drawings wherein like elements are numbered alike in the accompanying Figures.

DETAILED DESCRIPTION OF THE INVENTION

An embodiment of the invention provides the capability to sample ambient noises and dynamically adjust the x-ray exposure tone volume above the ambient noise by a determined amount. In an embodiment an audio receiver and a processor are configured to sample the ambient noise for a predetermined amount of time and apply that information to the exposure tone. In an embodiment, a tone detector can also sample the generated exposure tone and thus provide a diagnostic capability for a tone generator.

In an embodiment, an audio receiver is incorporated into the design of the device, receives audio inputs from the environment, and sends data representative thereof to the processor. This data is utilized to assign a volume level of the tone generator, such as when an exposure tone is required by the system. In an embodiment, the processor controls the tone generator. Further, in an embodiment, during tone generation, a feedback loop is configured to detect the tone itself, which serves to indicate that the tone generator is functioning properly.

Figure 1:
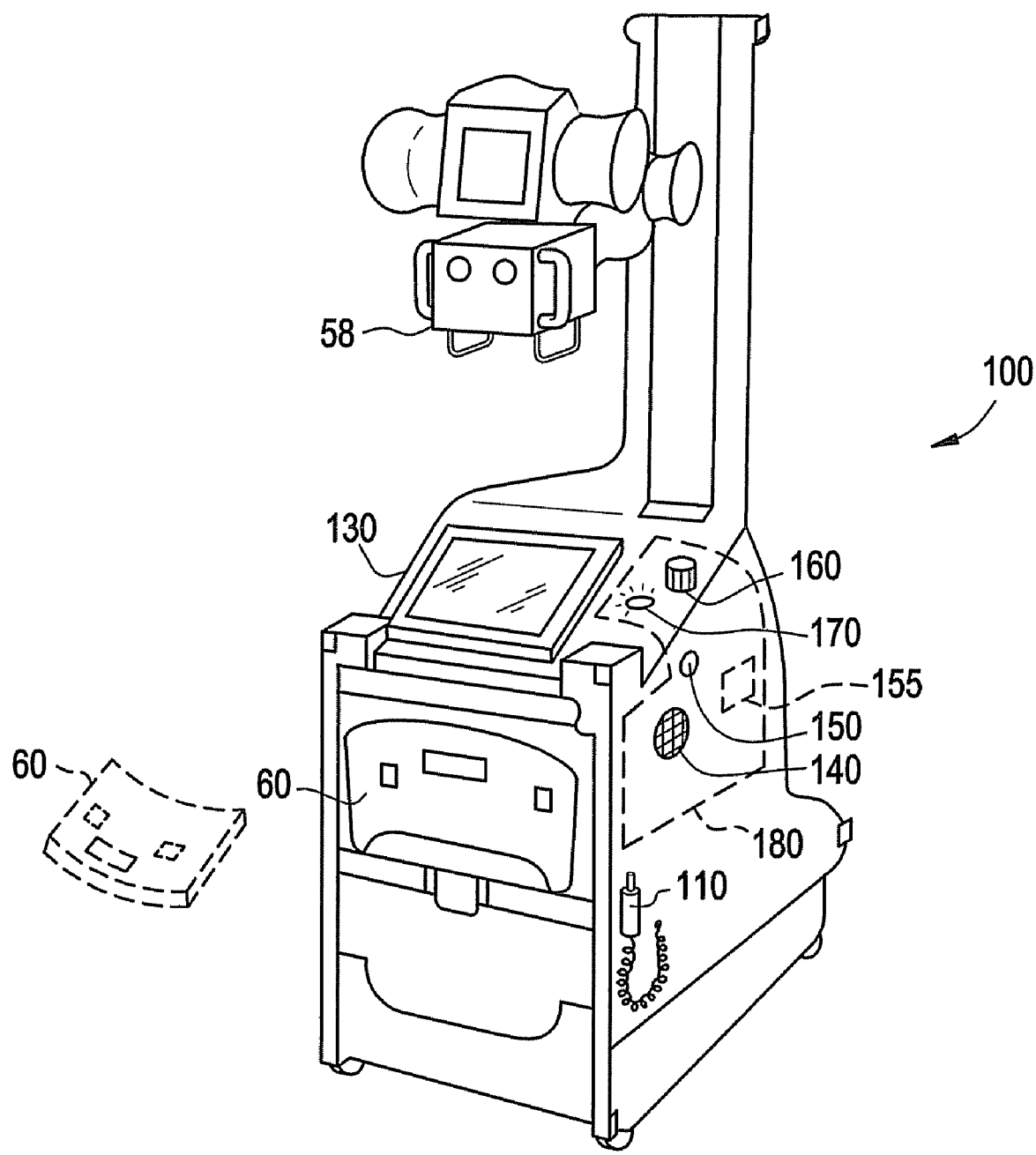
FIG. 1 depicts a schematic diagram of an exemplary x-ray system in accordance with an embodiment of the invention.

Referring now to FIG. 1, an exemplary embodiment of an x-ray system 100 is depicted. In an embodiment, the x-ray system 100 is a mobile x-ray system 100. An x-ray tube assembly 58 is configured to transmit x-ray radiation through an imaging object, such as a portion of human anatomy for example, toward a detector assembly 60 that is sensitive to the x-ray radiation, and positioned opposite the x-ray tube assembly 58. As the x-ray radiation from the x-ray tube assembly 58 passes through the imaging object, anatomy components of varying densities within the imaging object provide for differential x-ray attenuation. The differential x-ray attenuation results in an image on the detector assembly 60 that depicts the anatomy components within the imaging object. It will be appreciated that the detector assembly 60 is depicted in FIG. 1 in a storage and travel position, to allow for ease of portability of the mobile x-ray system 100, and that the detector assembly 60 is movable to other positions, such as one shown by the dashed lines, to be positioned opposite the x-ray assembly 58.

While an embodiment of the invention has been described as a mobile x-ray system, it will be appreciated that the scope of the invention is not so limited, and that the invention will also apply to other medical imaging systems that generate tones to indicate a status of the system, such as stationary x-ray systems, computed tomography (CT) systems, magnetic resonance (MR) systems, and ultrasound systems, for example.

An operator's x-ray console 130 is in signal communication with the x-ray tube assembly 58, the console 130 being configured to control the x-ray tube assembly 58. A handswitch 110 is in signal communication with the console 130 via a switch cord, and is configured to communicate with the console 130 to initiate the x-ray exposure by the x-ray tube assembly 120. In an embodiment, the handswitch 110 is configured to be held by an operator of the x-ray system 100. In an embodiment, the handswitch 110 is in signal communication with the x-ray console 130 via a wireless connection.

While an embodiment of the invention has been described having a handswitch in signal communication in conjunction with an x-ray console, it will be appreciated that the scope of the invention is not so limited, and that the invention will also apply to x-ray systems that use other methods to prepare the x-ray machine to take an exposure and initiate the exposure, such as button mounted directly on the console, for example.

When making an X-ray exposure, and as a result of industry regulations, an embodiment employs an audible indication, also herein referred to as a tone, to indicate transmission of x-rays. This is accomplished via a tone generator 140 located within the x-ray system 100. In an embodiment, the tone generator 140 is at least one of a buzzer, a piezo circuit, or other audio tone generator, for example. The tone generator 140 may also be coupled to at least one speaker. It will be appreciated that the preceding examples are provided for the purpose of illustration, and not limitation of the invention described herein.

A difficulty may arise if other equipment utilized in the vicinity of the x-ray system 100 generates tones that are similar to the tone generated by the x-ray system 100. Depending on the quantity, intensity, and frequency of the tones generated by other equipment, the tone of the x-ray system 100 may be difficult to distinguish. This difficulty may lead to uncertainty of the operator 150 regarding whether a tone has been generated by the x-ray system 100 to indicate transmission of x-rays, and that an exposure has occurred, or if the tone has been generated by other equipment within the environment.

It will be appreciated that an attempt to resolve the difficulty of distinguishing the tone by increasing the intensity or volume of the tone may result in generation of the tone that is objectionably loud to a patient, as well others within the vicinity of the x-ray system 100. Further, an excessive increase in the intensity or volume of the tone will only accentuate the ambient noise level of the environment in which the x-ray system 100 is used.

In an embodiment, the x-ray system 100 includes a status indication device, represented by the components within the box indicated by reference numeral 180, configured for use in the x-ray system 100. The status indication device 180 includes an audio receiver 150, a tone generator 140, a processor 155, an adjustment mechanism 160, and at least one speaker. The status indication device 180 may also include a visual indicator 170. The audio receiver 150 is coupled to the processor 155, and is configured and disposed to collect audio information surrounding and associated with the x-ray system 100. In an embodiment, the collected audio information includes ambient audio information, also hereinafter referred to as background noise, such as the sounds that may be present in the environment surrounding the x-ray system 100. Examples of ambient audio information include, but are not limited to, background conversations of people near the x-ray system 100, tones that may be generated by other pieces of equipment near the x-ray system 100, noise created by transportation of equipment nearby, and the sound of operating motors of equipment such as ventilators and intravenous pumps, for example. In an embodiment, the collected audio information comprises audio information of the audio tone from the x-ray system, as will be discussed further below.

In an embodiment, the processor 155 is configured to be receptive of a signal representative of the audio information collected by the audio receiver 150. The processor 155 is configured to evaluate the properties of the background noise, and develop a set of audio properties for the audio tone used to indicate the occurrence of an x-ray exposure from the x-ray system 100, that cause the audio tone to be distinguishable from the collected background noise. In an embodiment, the processor 155 is configured to evaluate the properties of the background noise, and develop a set of audio properties that include at least one of the intensity of the audio tone, the frequency of the audio tone, the volume of the audio tone, the duration of the audio tone, and the ability to provide a non-continuous, or pulsating tone such that the tone is capable to be distinguished from the background noise in the environment surrounding the x-ray system 100. In an embodiment, the adjustment mechanism 160 is coupled to the tone generator 140 and the processor 155, and is configured for dynamically developing, or changing, the set of audio properties that cause the audio tone to be distinguishable from the collected audio information.

While an embodiment of the invention has been described with an adjustment mechanism depicted as an external control, it will be appreciated that the scope of the invention is not so limited, and that the invention will also apply to x-ray systems that have adjustment mechanisms that may be an internal controls, for example.

In an embodiment, the processor 155 is a microprocessor. While an embodiment of the invention has been described having a microprocessor, it will be appreciated that the scope of the invention is not so limited, and that the invention will also apply to x-ray systems that have alternate processing means, such as a micro-controller, a field programmable gate array (FPGA), and any element appropriate for performing the processing tasks disclosed herein, for example.

In an embodiment, the tone generator 140 is coupled to and responsive to the processor 155, and is configured to generate the audio tone in response to a defined status of the x-ray system 100. In an embodiment, the defined status includes transmission of x-ray radiation by the x-ray system, such as in response to activation of the exposure switch on the handswitch 110, for example. In another embodiment, the defined status includes preparation of the x-ray system 100 for the exposure, or transmission of x-ray radiation. In an embodiment, the processor 155 is configured to define more than one set of audio properties of the tone to indicate more than one status of the x-ray system. In an embodiment, the processor 155 is configured to allow user selection of the audio properties of the audio tone to indicate the status of the x-ray system 100. In an embodiment, the processor 155 is configured to provide to the user, for selection, at least one tone that has been developed to be distinguishable from the background ambient noise. This will allow the user to select a tone that they may be able to more easily distinguish from the background noise.

In an embodiment, the audio receiver 150 is configured to collect the audio information of the audio tone, and provide to the processor 155 for evaluation the audio information of the audio tone. It will be appreciated that in an embodiment, collection of the audio information of the audio tone will allow the processor 155 to confirm that the audio information of the audio tone has successfully been generated having the developed set of audio properties to allow it to be distinguishable from the ambient audio information, or background noise.

It will be appreciated that failure of the tone generator 140 to generate the audio tone with the set of audio properties developed by the processor 155 is likely to indicate the need for service of the tone generator 140. In an embodiment, the processor 155 is configured to compare the audio properties of the actual tone generated with the set of audio properties developed by the processor 155, to determine if the audio information of the audio tone indicates the need for service of the tone generator 140. In an embodiment, the visual indicator 170 is responsive to the processor 155, and the processor 155 is configured to activate the visual indicator 170 in response to determining that the audio information of the audio tone indicates the need for service of the tone generator 140.

In another embodiment, the processor 155 is configured to evaluate the collected audio information to determine if the collected audio information indicates a need for service of the x-ray system 100. In an embodiment, the processor 155 will evaluate the occurrence, frequency, intensity, and trends of collected audio information, to determine if the audio information is created by the x-ray system 100, and if it is changing in such a manner as to indicate the increasing likelihood of a potential service need, such as if a wheel of the mobile unit is squeaky, and an anode rotation motor is generating a greater than acceptable amount of noise, for example. In an embodiment, the processor 155 is configured to activate the visual indicator 170 in response to determining that the collected audio information indicates the need for service. It will be appreciated that as a result of this diagnostic capability, the status indication device 180 is contemplated to allow predictive maintenance to be performed on the x-ray system 100, thereby reducing costs associated with reduced availability caused by unexpected service needs. While an embodiment of the invention has been depicted having a light as a visual indicator, it will be appreciated that the scope of the invention is not so limited, and that the invention will also apply to x-ray systems that have other visual indicators, such as a message on an operation screen, an indicator configured to change color, and wheel configured to rotate to indicate the need for service, for example.

Figure 2:
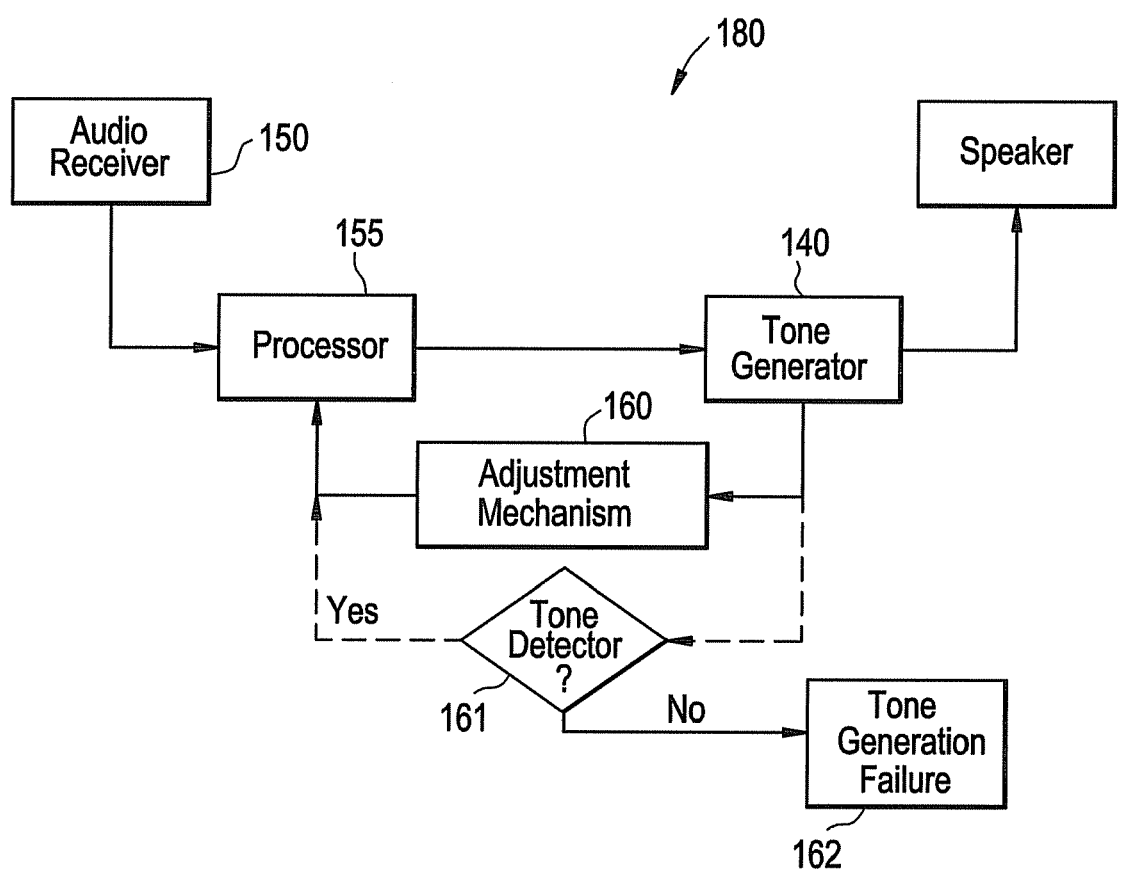
FIG. 2 depicts a block diagram of an exemplary system in accordance with an embodiment of the invention.

Referring now to FIG. 2, a block diagram representing the components and operation of the status indication system 180 is depicted. In an embodiment, the audio receiver 150 is configured to receive audio information surrounding the x-ray system 100, including the tone that has been created by the tone generator 140. The audio information is made available to the processor 155, which is configured to evaluate the audio information and to determine a set of audio properties of at least one tone that will be distinguishable from the background ambient noise. The processor 155 is configured, in response to the appropriate status of the x-ray system 100, to initiate the generation of the audio tone by the tone generator 140, such that the tone will be distinguishable from the background ambient noise. In an embodiment, the speaker is responsive to the tone generator 140 to create the tone.

In an embodiment, the adjustment mechanism 160 is configured to allow the user to dynamically change at least one of the set of audio properties determined by the processor 155 to distinguish the audio tone from the background ambient noise. In an embodiment, the audio receiver 150, and the processor 155, are configured to perform as a tone detector 161 to evaluate proper operation of the tone generator 140. That is, in an embodiment, the audio receiver 150 and the processor 155 are configured to evaluate the audio properties of the tone generated by the tone generator 140 to confirm that it is able to be distinguished from the background noise. In an embodiment, in response to determining that the tone is not able to be distinguished from the background noise, the processor 155 is configured to initiate a tone generation failure signal 162. In an embodiment, the initiation of the tone generation failure signal 162 is configured to activate the visual indicator 170.

Figure 3:
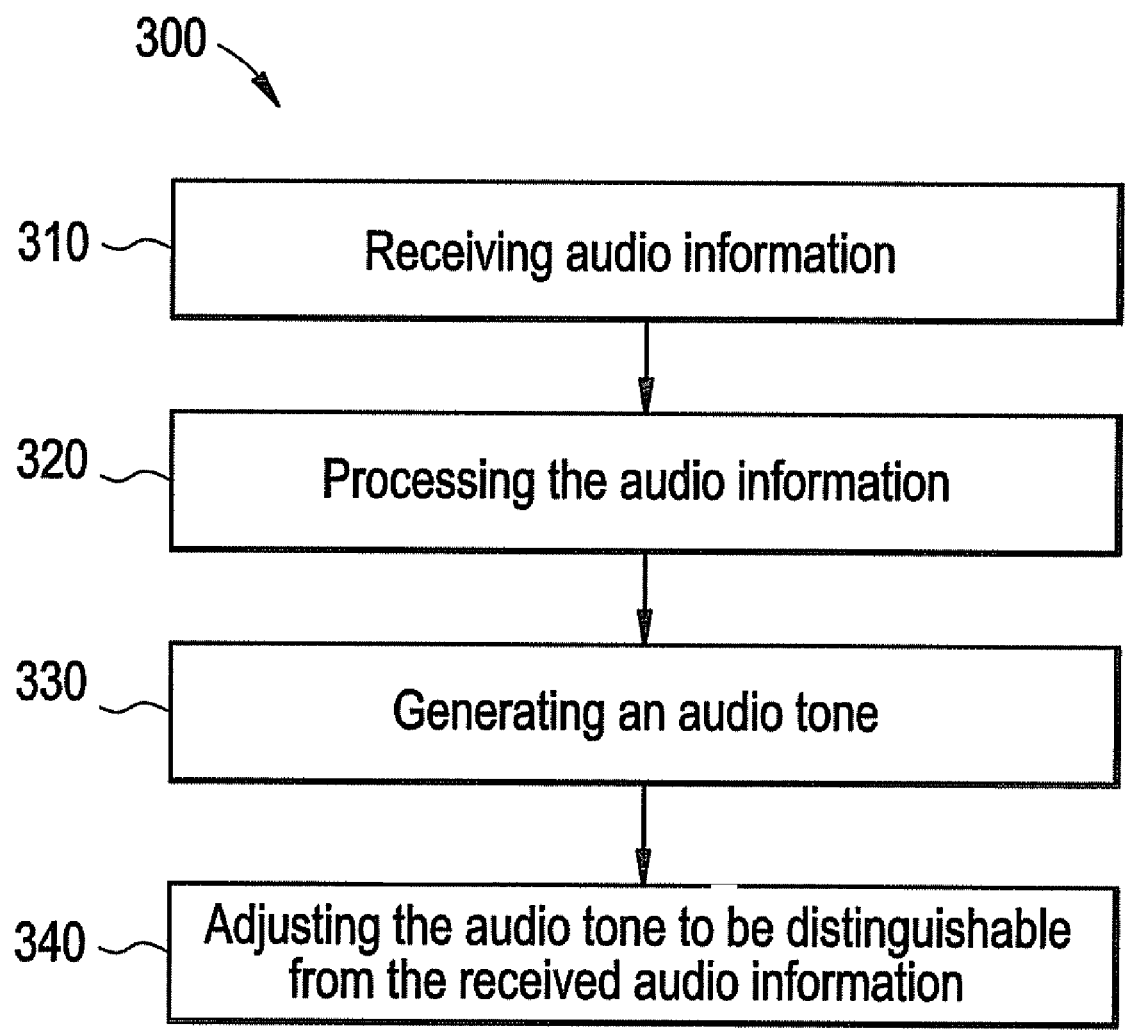
FIG. 3 depicts a flowchart of an exemplary method in accordance with an embodiment of the invention.

In view of the foregoing, the x-ray system 100 performs the method of system status indication. Referring now to FIG. 3, a flowchart 300 of an embodiment of the method is depicted.

In an embodiment, the method includes receiving 310 audio information surrounding and associated with the x-ray system 100, processing 320 the audio information, and generating 330 an audio tone responsive to the processing of the audio information. The method further includes adjusting 340 the audio tone to be distinguishable from the received audio information. In an embodiment, the receiving audio information surrounding and associated with the x-ray system comprises receiving audio information of the audio tone associated with the x-ray system. In an embodiment, the method further includes determining if there is a tone generation failure.

As disclosed, some embodiments of the invention may include some of the following advantages: the ability to provide a status indication tone that is distinguishable from the ambient background noise; the ability to confirm proper operation of the tone generator; the ability to provide preventive maintenance service information; the ability to allow a user to select a specific tone; and the ability to reduce system down time from unexpected service needs.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A status indication device configured for use in an x-ray system, the device comprising:
   an audio receiver configured and disposed to collect audio information surrounding and associated with the x-ray system;
   a processor coupled to the audio receiver receptive of a signal representative of the collected audio information;
   a tone generator coupled and responsive to the processor and configured to generate an audio tone in response to a defined status of the x-ray system; and
   an adjustment mechanism coupled to the tone generator and the processor for dynamically developing a set of audio properties that cause the audio tone to be distinguishable from the collected audio information.

2. The device of claim 1, wherein:
   the collected audio information comprises ambient audio information surrounding and associated with the x-ray system.

3. The device of claim 2, wherein:
   the collected audio information comprises audio information of the audio tone; and
   the processor is configured to confirm that the audio information of the audio tone is distinguishable from the ambient audio information.

4. The device of claim 3, further comprising:
   a visual indicator responsive to the processor;
   wherein the processor is configured to determine if the collected audio information indicates a need for service of the x-ray system; and
   wherein the processor is configured to activate the visual indicator in response to determining that the collected audio information indicates the need for service of the x-ray system.

5. The device of claim 4, wherein:
   the processor is configured to determine if the audio information of the audio tone indicates the need for service of the tone generator; and
   the processor is configured to activate the visual indicator in response to determining that the audio information of the audio tone indicates the need for service of the tone generator.

6. The device of claim 1, wherein:
   the set of audio properties comprise at least one of intensity of the audio tone, frequency of the audio tone, volume of the audio tone, and duration of the audio tone.

7. The device of claim 1, wherein:
   the processor is configured to allow user selection of the set of audio properties.

8. The device of claim 1, wherein:
   the x-ray system is a mobile x-ray system.

9. The device of claim 1, wherein:
   the defined status comprises transmission of x-ray radiation by the x-ray system.

10. The device of claim 1, wherein:
    the defined status comprises preparation for a transmission of x-ray radiation by the x-ray system.

11. An x-ray system configured to provide x-ray images of a subject, the system comprising:
    an x-ray tube assembly configured to transmit x-ray radiation;
    an x-ray detector assembly positioned opposite the x-ray tube assembly for detection of x-rays transmitted through the subject;
    an audio receiver configured and disposed to collect audio information surrounding and associated with the x-ray system;
    a processor coupled to the audio receiver receptive of a signal representative of the collected audio information;
    a tone generator coupled to and responsive to the processor and configured to generate an audio tone in response to a defined status of the x-ray system; and
    an adjustment mechanism coupled to the tone generator and the processor for dynamically developing a set of audio properties that cause the audio tone to be distinguishable from the collected audio information.

12. The system of claim 11, wherein:
    the status comprises transmission of x-ray radiation by the x-ray system.

13. The system of claim 11, wherein:
    the processor is configured to allow user selection of the set of audio properties.

14. The system of claim 11, wherein:
    the collected audio information comprises ambient audio information surrounding and associated with the x-ray system.

15. The system of claim 14, wherein:
    the collected audio information comprises audio information of the audio tone; and
    the processor is configured to confirm that the audio information of the audio tone is distinguishable from the ambient audio information.

16. The system of claim 15, further comprising:
    a visual indicator responsive to the processor;
    wherein the processor is configured to determine if the collected audio information indicates a need for service of the x-ray system; and
    wherein the processor is configured to activate the visual indicator in response to determining that the collected audio information indicates the need for service of the x-ray system.

17. The system of claim 16, wherein:
    the processor is configured to determine if the audio information of the audio tone indicates the need for service of the tone generator; and
    the processor is configured to activate the visual indicator in response to determining that the audio information of the audio tone indicates the need for service of the tone generator.

18. A system for use in an x-ray system, the system comprising:
    means for receiving audio information surrounding and associated with the x-ray system;
    means for processing the audio information, the means for processing the audio information being receptive of a signal representative of the collected audio information;
    means for generating an audio tone responsive to the processing means in response to a defined status of the x-ray system; and means for adjusting the audio tone by developing a set of audio properties that cause the audio tone to be distinguishable from the collected audio information.

19. The system of claim 18, wherein:
the collected audio information comprises ambient audio information surrounding and associated with the x-ray system and audio information of the audio tone; and
the means for processing the audio information further comprises means for confirming that the audio information of the audio tone is distinguishable from the ambient audio information.

20. The system of claim 19, further comprising:
a visual indicator responsive to the means for processing;
wherein the means for processing the audio information further comprises means for determining if the audio information of the audio tone indicates a need for service of the means for generating the audio tone;
wherein the means for processing the audio information further comprises means for activating the visual indicator in response to determining that the audio information of the audio tone indicates the need for service of the means for generating the audio tone.

21. A method for use in an x-ray system, the method comprising:
receiving audio information surrounding and associated with the x-ray system;
processing the audio information;
generating an audio tone responsive to the processing of the audio information; and
adjusting the audio tone to be distinguishable from the received audio information.

22. The method of claim 21, wherein receiving audio information surrounding and associated with the x-ray system comprises receiving audio information of the audio tone associated with the x-ray system.

23. The method of claim 22, further comprising:
determining if there is a tone generation failure.

* * * * *